United States Patent [19]

Nadeau et al.

[11] Patent Number: 4,534,219

[45] Date of Patent: Aug. 13, 1985

[54] ACOUSTIC DETECTION OF CRACKS IN METAL PIECES

[76] Inventors: François Nadeau, 822 Yvonne Duckett St., St-Bruno, Quebec, Canada, J3V 4P6; Jean F. Bussiere, 155 Ave. Lakeview, St-Bruno, Quebec, Canada, J3V 2L6; Ghislain Vaudreuil, 437 Brion, Boucherville, Quebec, Canada, J4B 6B2

[21] Appl. No.: 552,973

[22] Filed: Nov. 17, 1983

[51] Int. Cl.$^3$ ............................................. G01N 29/04
[52] U.S. Cl. ......................................... 73/587; 73/799
[58] Field of Search ................. 73/587, 579, 801, 799, 73/12

[56] References Cited

U.S. PATENT DOCUMENTS

| | | | |
|---|---|---|---|
| 3,284,192 | 11/1966 | Larson et al. | 75/130 |
| 4,020,678 | 5/1977 | Laue | 73/67.2 |
| 4,091,660 | 5/1978 | Yanagi | 73/658 |
| 4,122,723 | 10/1978 | Levizzari et al. | 73/579 |
| 4,285,241 | 8/1981 | Smith et al. | 73/572 |
| 4,375,762 | 3/1983 | Yanagisawa et al. | 73/12 |

*Primary Examiner*—Anthony V. Ciarlante

[57] ABSTRACT

An acoustic crack detection method and device in which an impact is produced between an actually tested metal piece and an anvil. This impact generates an acoustic wave formed of a plurality of components, one of these wave components being produced by vibrations of the metal piece and having a frequency indicating a cracked or uncracked state of this piece. A microphone senses the acoustic wave generated by the impact and a measuring circuit receives the signal from the microphone for measuring the energy, within a predetermined time gate and within a predetermined frequency bandwidth, of the wave component of interest. The measured energy is compared with a reference level in order to determine if the actually tested metal piece is cracked or not. Of course, the anvil is designed so that its vibrations produced by the impact generate no wave component at a frequency included within the predetermined frequency bandwidth, whereby the crack detection is not disturbed by any acoustic wave component generated by the anvil. The detecting device may be used in an apparatus for sorting cracked and uncracked metal pieces.

24 Claims, 9 Drawing Figures

ACOUSTIC DETECTION OF CRACKS IN METAL PIECES

BACKGROUND OF THE INVENTION

1. Field of the Invention

The present invention relates to a method and a device for acoustically detecting cracks in metal pieces having a same shape and made of a same metal, for example hardened steel grinder balls, which detecting method and device may be used respectively in a method and a device for automatically sorting out the cracked metal pieces.

2. Description of the Prior Art

Regarding specifically hardened steel grinder balls, it has been reported by manufacturers of such hardened steel grinder balls for ball mills that a non-negligeable percentage of the balls produced exibit deep cracks, and therefore tend to rupture under operating conditions inside the ball mill. This problem is familiar to ball mill operators who often have shut the mill down to remove the broken ball pieces from inside the mill to ensure smooth operating conditions of the mill and to prevent excessive wear of the inner sleeve of such a ball mill. This unpleasant, time consuming job obviously raises the production costs.

The present method used to limit the number of cracked grinder balls introduced in the ball mill is to sort them out manually. According to this present method, the cracks in the grinder balls can be detected both visually and acoustically. The acoustic detection of cracks can be carried out by knocking together two grinder balls. If at least one of these two balls knocked together is cracked, a characteristic high pitch sound is generated, which high pitch sound can be recognized by the operator.

However, such a manual inspection is very costly if compared with the low profit margin obtained for this kind of crude product, namely hardened steel grinder balls. Inspection of each and every grinder ball would be therefore prohibitive. At the present time, only samples retained from each batch of produced grinder balls are inspected in order to give a statistical estimate of the percentage of cracked balls in each particular batch of produced grinder balls. This limited sorting is expensive to the manufacturers, gives only an estimated percentage of cracked balls and does not provide any real time control of quality on the line of production of the grinder balls.

In U.S. Pat. No. 3,284,192 granted to GENERAL MOTORS CORPORATION on Nov. 8, 1966, it is described a device to evaluate mechanical properties of the material a cast metal piece. This evaluation of the mechanical properties of the cast piece is based on an accurate acoustic measurement of the vibration resonance frequency of this cast piece. In order to measure this resonance frequency, the cast piece has to be mounted on a sponge rubber base and thereafter to be stroken by a mallet. It is evident that the design of this prior art device is specifically adapted to evaluate mechanical properties of the material of a cast piece by measuring the vibration resonance frequency of this piece. Moreover, it does not provide a very simple method of detecting cracks in metal pieces and it requires a mounting of the tested pieces on the rubber base.

U.S. Pat. No. 4,122,723 granted to FIAT SOCIETA PER AZIONI on Oct. 31, 1978, proposes a device for testing finished part using transducers and accelerometers to induce the measure vibrations in the tested part, which has to be rigidly mounted on a mechanical assembly. Again, the measurement carried out by this testing device is relatively complex and the tested piece must be closely coupled with the transducers and accelerometers of the device.

U.S. Pat. No. 4,020,678 dated May 3, 1977, describes a device for testing the teeth of a gear. This prior art device comprises an electromagnet for generating a magnetic field pulse to induce a vibration to each gear tooth and a circuit to detect this vibration and to analyze the amplitude and frequency of the vibration of the gear tooth. The electromagnet must be coupled in sequence with each gear tooth and therefore such a device does not allow a relatively high rate (metal pieces per time unit) of testing operations. Moreover, the measurement carried out by this testing device is relatively complicated due to the required analysis of amplitude and frequency of the vibration of the gear tooth.

SUMMARY OF THE INVENTION

An object of the present invention is therefore to provide a very simple device for detecting cracks in metal pieces having a same shape and made of a same metal, for example hardened steel grinder balls, which detecting device being suitable for testing metal pieces on the line of production of these pieces.

Another object of the present invention is to provide a device for detecting cracks in metal pieces using a principle of acoustic detection of cracks based on the above-mentioned acknowledgment that the acoustic waves produced by impacts of cracked and uncracked metal pieces, for example grinder balls, have reproducible differences which can be detected by an appropriately designed detecting device.

More particularly, according to the present invention, there is provided a device for detecting a crack in a metal piece comprising:

anvil means;

means producing an impact between the metal piece and the anvil means, said impact generating an acoustic wave formed of a plurality of components, one of said components being produced by vibrations of said metal piece and having a frequency indicating a cracked or uncracked state of the metal piece;

means for sensing and measuring the energy of said one component of said generated acoustic wave within a predetermined time gate and within a predetermined frequency bandwidth; and means for determining if said metal piece is cracked or uncracked in accordance with said measured energy;

said anvil means being designed so that its vibratitons generated by the impact produce no acoustic wave component at a frequency located within said predetermined frequency bandwidth in order to prevent influence on said energy measurement of any component of said generated acoustic wave produced by the anvil means.

According to another aspect of the invention, there is provided a device for sorting cracked and uncracked metal pieces having a same shape and made of a same metal, comprising:

the detecting device defined hereabove;

means for supplying in sequence to the impact producing means for the detecting device the metal pieces for detecting through said detecting device if these metal pieces are cracked or uncracked; and
means controlled by the determining means of the detecting device for conducting each cracked metal piece from the detecting device towards first storing means and for conducting each uncracked metal piece from the detecting device towards second storing means.

According to a further aspect of the invention, there is provided a method for detecting a crack in a metal piece comprising the steps of:
producing an impact between the metal piece and anvil means, said impact generating an acoustic wave formed of a plurality of components, one of said components being produced by vibrations of said metal piece and having a frequency indicating a cracked or uncracked state of the metal piece;
sensing and measuring the energy of said one component of said generated acoustic wave within a predetermined time gate and within a predetermined frequency bandwidth, and
determining if said metal piece is cracked or uncracked in accordance with said measured energy; said anvil means being designed so that its vibrations generated by the impact produce no acoustic wave component at a frequency located within said predetermined frequency bandwidth in order to prevent influence on said energy measurement of any component of said generated acoustic wave produced by the anvil means.

According to another further aspect of the present invention, there is provided a method for sorting cracked and uncracked metal pieces having a same shape and made of a same metal, comprising the steps of:
carrying out in sequence for each metal piece the above-defined detecting method for detecting if this metal piece is cracked or uncracked; and
conducting each metal piece found cracked by the determining step of the detecting method towards first storing means, and conducting each metal piece found uncracked by the determining step of the detecting method towards second storing means.

BRIEF DESCRIPTION OF THE DRAWINGS

The objects, advantages and other features of the present invention will become more apparent from the following non restrictive description of a preferred embodiment thereof directed specifically to the detection of cracks in hardened steel grinder balls, made in conjunction with the accompanying drawings in which.

DETAILED DESCRIPTION OF THE PREFERRED EMBODIMENT

The following explanations with reference to FIGS. 1 to 4 of the drawings are for the purpose of describing in details the principle of acoustic detection of cracks in grinder balls, which principle is used in the present invention, before proposing a device for carrying out into practice the above-mentioned acoustic detection.

Figure 1A:
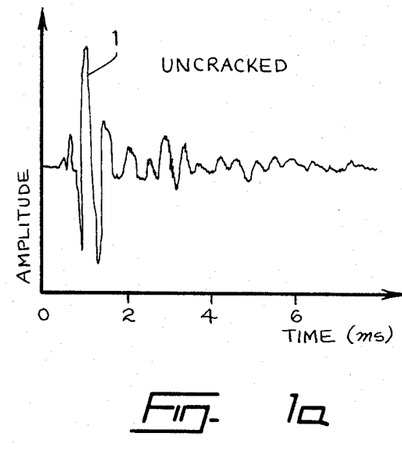
FIGS. 1A and 1B are examples of typical acoustic waveforms generated by impacts of cracked and uncracked hardened steel grinder balls, respectively.
Figure 1B:
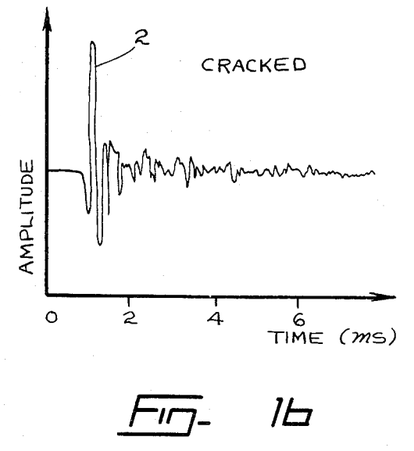

When two grinder balls are knocked together in ambient air, an impact acoustic wave is generated, which impact wave has several distinct features. FIGS. 1A and 1B show two typical waveforms picked up by an appropriate microphone and captured on a digital waveform analyzer. The waveform shown on FIG. 1A was produced by an impact between two uncracked balls while the waveform of FIG. 1B was produced by an impact between an uncracked and a cracked ball. The balls were hand held with one of the two balls forming a target ball held near the microphone on one side and the other ball forming an <<anvil>> ball, always constituted by an uncracked ball, on the opposite side. A close examination of these two waveforms reveals several distinct features. First of all, an initial pulse 1 or 2 is always present at the beginning of each waveform, whether the balls are cracked or not. Also common to both waveforms is the low frequency rumble that follows. This rumble is due to reflections on surrounding room structures and low frequency room resonances. Following the initial pulse and low frequency rumble, high frequency resonances are present in both waveforms. In the case of the impact waveform, produced by the two uncracked balls (FIG. 1A), the amplitude of the resonance is small, its frequency is around 40 kHz and its damping is low. In the case of the impact waveform produced by a cracked ball and an uncracked ball (FIG. 1B), the amplitude of the resonance is much greater, while its frequency is lower (around 5–15 kHz) and it is heavily damped.

The initial pulse having a width around 200 μs such as the pulses 1 and 2 of FIGS. 1A and 1B appears at the beginning of every waveform produced by grinder ball impacts, whether uncracked or cracked balls are knocked. This relatively low frequency pulse (always <3 kHz) has no relation with the resonance frequencies of the grinder balls producing the impact, but can be explained by considering the overall motion of the grinder balls during an impact as a source of acoustic waves in air, as will appear more clearly upon reading of the following description.

It is known in theory that the relation between a displacement $\epsilon$ of a particle and acoustic pressure p for plane waves on air can be expressed as follows:

$$p = \rho_o c \frac{\delta \epsilon}{\delta t} \quad (1)$$

where
- $\rho_o$ is the density of air,
- c is the velocity of sound in air, and
- $\delta\epsilon/\delta t = \mu$, the particle velocity.

Thus an infinite flat surface moving in air at a velocity $\mu(t)$ will generate a pressure wave p(t) as given by Eq. (1), considering that the particles in contact with the flat surface have the same displacement. For spherical surfaces, one can no longer assume plane waves which means that a directivity factor along with a radial dependence on amplitude would appear. Still the time dependence of $\mu(t)$ and p(t) would essentially be the same for points very near the surface. It can therefore be considered that when a grinder ball is struck by another grinder ball, it is accelerated and its front face generates a compressive acoustic wave while its back face generates a rarefaction acoustic wave.

This assumption can be easily verified experimentally in the case of a grinder ball which is accelerated as it is struck by another grinder ball: if a microphone is placed near the front face of the target grinder ball, it senses a positive pressure pulse. The ball thus acts as a dipolar source of length approximately equal to the diameter of the ball.

This latter assumption can also be verified experimentally by measuring the width of such low frequency pulses obtained using grinder balls of various diameter. In this experiment, a microphone is placed on the collision axis, near the front face of the target grinder ball. The experiment shows that the fall in pressure produced at the back face of the target ball is delayed with regards to the rise in pressure at the front face of this ball by the propagation time of acoustic waves over a distance equal to the diameter <<d>> of the grinder ball, thus producing a positive pulse of width Δt equal to d/c, where c is the velocity of sound in air as mentioned above.

An important aspect to determine with respect to these low frequency pulses is the frequency spectrum of these pulses, in order to filter them while performing measurements, as will be explained in more details hereinafter.

For this purpose one can look at the shape of the pulse and relate it to the time evolution of the velocity of the ball. In particular, the rise time of the pulse is expected to be equal to the rise time of the velocity of the ball, i.e. the frequency content of the pulse would be limited by the interaction time T of the collision.

For verifying this assumption, it is possible to calculate this interaction time T for the simple case of two solid spheres of diameter d and mass m colliding at a velocity $v_o$ (the relative velocity of one sphere with regards to the second one is 2. $v_o$).

Figure 2:
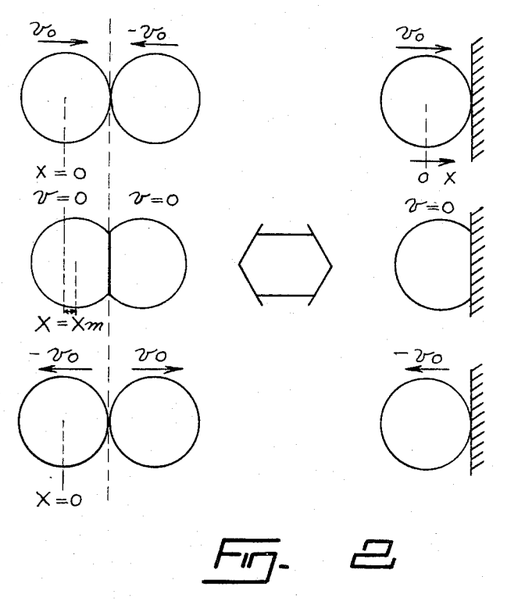
FIG. 2 shows schematically the symmetry of a collision between two similar massive spheres having equal but opposite velocities.

As the collision of two massive spheres having equal but opposite velocities presents a symmetry as shown on FIG. 2, one of the two spheres can be replaced with a fixed and infinitely rigid wall for analysis purposes. With the position of the remaining ball x=0 and time t=0 chosen when the sphere touches the wall (see FIG. 2), the position x of the ball in time may be approximated by the following equation of motion of the ball during an impact with the wall:

$$x \cong x_m \sin \omega t \quad (2)$$

where $x_m$ is the maximum value of the position of the ball x and can be expressed as follows:

$$x_m = 1.422 \left[ \frac{m^2 v_o^4}{E^2 d} \right]^{1/5} \quad (3)$$

where E is the modulus of elasticity of the material of the sphere.

Knowing that when t=0, $dx/dt = v_o$, we have: $\omega = v_o/x_m$ see equation 2.

Of course, the interaction time T of the collision corresponds to a half cycle of the sine wave and can be expressed as:

$$T = \pi/\omega$$
$$= \pi x_m/v_o$$

Thus, finally:

$$T = 4.467 \left[ \frac{m^2}{E^2 d v_o} \right]^{1/5} \quad (6)$$

In using the following numerical values:

m = 1.8 kg d = 76 mm ≅ 3"

E = 2 × 10⁵ MPa $v_o \cong 1$ m/s we obtain:

T ≅ 280 μs.

This value obtained theorically is in good agreement with the experimental data (see FIGS. 1A and 1B) and offers an appropriate explanation to the absence of frequency components higher than 2–3 kHz in the initial pulse, which pulse can therefore be easily filtered. However, as this initial pulse also generates harmonic components, it is preferable to carry out a filtering up to about 10 kHz to completely filter the wave components related to the initial pulse.

The low frequency rumble can also be eliminated by producing the grinder ball impacts within an echo-free chamber.

Figure 3:
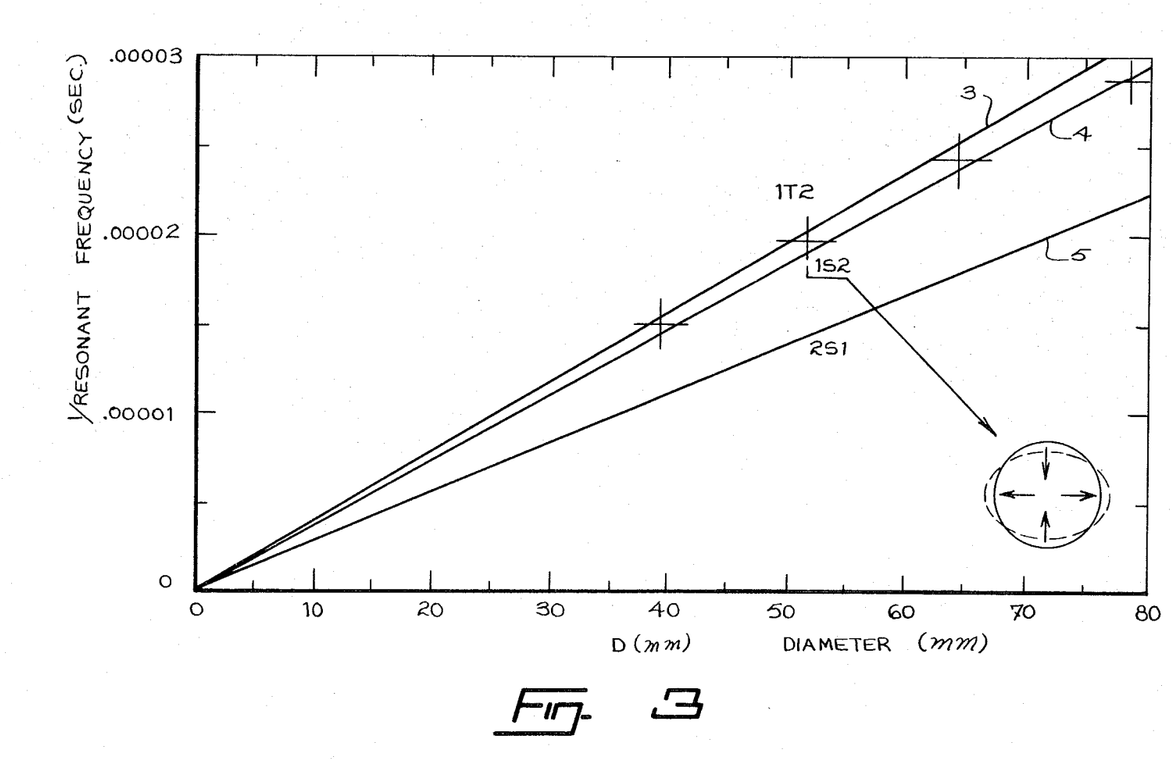
FIG. 3 is a plot of the inverse of the vibration resonance frequency of uncracked grinder balls as a function of the ball diameter, in which the straight lines represent theoretical curves for the three first modes of vibrations of solid steel spheres, this figure showing also the vibration movement of an uncracked grinder ball.

Sound measurements of uncracked grinder ball impacts can be made using a high pass filter to attenuate the low frequency noise associated with the initial pulse (up to 3 kHz). In this case, the filtered signals show the enhanced presence of a high frequency resonance in the acoustic waveform ranging from 35 kHz for a 75.4 mm ≅ 3" diameter grinder balls to 65 kHz for 37.7 mm ≅ 1½" diameter grinder balls. This resonance oscillation can be related to one of the lower theoretical modes of resonance of a solid steel sphere. FIG. 3 is a plot of the inverse of the resonance frequency of uncracked grinder balls as a function of the ball diameter (see the points on the plot). The straight lines 3, 4 and 5 represent respectively theoretical curves for the three first theoretical modes of vibration 1T2, 1S2 and 2S1 for solid steel spheres calculated for hardened steel. All other modes fall below the 2S1 mode and so are not considered. A comparison between theoretical curves 3, 4 and 5 and the experimental points shown on FIG. 3 indicates that either the 1S2 mode or the 1T2 mode is the one that generates the high frequency acoustic waves. However, for torsional or <<T>> modes in spheres, as there is no radial displacement for such modes it is therefore assumed that these modes do not radiate any sound or acoustic wave in air. Only spheroidal or <<S>> resonance modes in spheres can therefore couple with air and generate an acoustic wave so that the 1S2 mode is obviously the one responsible for the high frequency tone produced by impacts of uncracked grinder balls as can be deduced from FIG. 3. A representation of the displacement associated with the 1S2 mode is also included in FIG. 3 which shows that this mode is very subject to be strongly exited by an impact because an impact produces an uniaxal force which ovally deforms the sphere. Other modes are also probably exited as well, including higher <<S>> modes. Some inharmonic distortion can indeed be observed on several high frequency waveforms. This is expected if other <<S>> modes are exited since their frequencies are not exact multiples of each other.

When acoustic measurements similar to those above are made using cracked grinder balls, an appearance of oscillations of medium range frequencies (5–15 kHz) in the waveforms is observed. These oscillations look like heavily damped resonance. A disappearance of the above-mentioned high frequency 1S2 vibration is also observed, especially for severely cracked balls for which the amplitude of the mid-range resonances is often the highest. This amplitude also depends on the point of impact, i.e. the orientation of the cracked ball relative to the anvil, i.e. the ball or other object on which it is struck. This effect however varies from one cracked ball to another and no reproducible pattern emerged.

Figure 4:
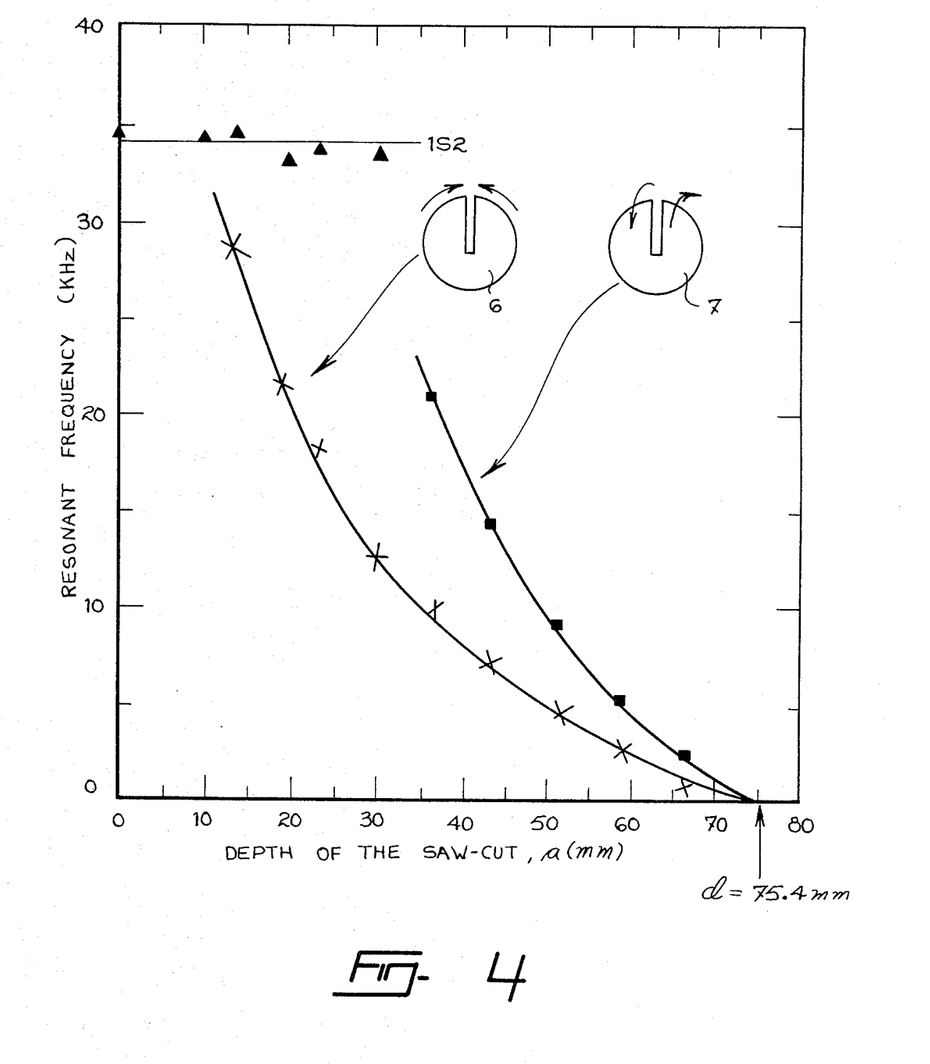
FIG. 4 is a plot of the resonance frequency of saw-cut grinder balls as a function of the depth of the saw-cut, this figure showing also the possible resonance modes of saw-cut grinder balls.

An explanation for this phenomenon is that the mid-range resonances, characteristic of cracked grinder balls, are attributed to some sort of <<tuning fork>> mode of vibration as the ball is partially divided by deep running cracks. For example, acoustic measurements made on artificially flawed grinder balls (saw-cut) reveal the presence of at least two modes of vibration at frequencies lower than the 1S2 mode of a solid uncracked ball or sphere. Experimental data for a 75.4 mm≅3″ grinder ball are presented in FIG. 4 which shows that the frequencies of the various resonances vary with the depth, a, of the saw-cut. We see that mid-range frequencies similar to those produced by naturally cracked balls appear for values of the depth of the saw-cut in the range of 30% to 70% of the diameter d of the grinder ball. The amplitude of the oscillation in the 1S2 mode becomes unmeasurable when the depth of the saw-cut a reaches about half the diameter of the ball. Displacements corresponding to the two <<tuning fork>> modes are illustrated at 6 and 7 in FIG. 4. This is in agreement with the observed experimental variations in the relative amplitude of the two frequencies with the orientation of the impact: when directed perpendicular to the plane of the saw-cut, the lower frequency mode shown at 6 in FIG. 4 is preferably exited whereas when directed parallel to the bottom of the saw-cut, the higher frequency <<shear>> mode shown at 7 on FIG. 4, is preferably excited. The frequency of both of these modes understandably tends towards zero when the value of the depth of the saw-cut approaches the value d of the diameter of the grinder ball.

Finally, one can verify that resonances of saw-cut balls were practically undamped compared to those of naturally cracked balls. Evidently, the latter are heavily damped by friction occurring along the crack interfaces. In consequence, one can also assume that the shear motion depicted at 7 in FIG. 4 for the <<shear>> mode is unlikely to occur in naturally cracked balls because of the friction, for which cracked balls the resonance mode shown at 6 in FIG. 4 is predominant.

As set forth hereinabove, noticeable differences exist between the acoustic wave produced by the impact of an uncracked grinder ball and the acoustic wave produced by the impact of a cracked grinder ball. It is therefore possible to electronically detect cracked grinder balls by detecting and measuring acoustic energy of the acoustic wave produced by the impact of a grinder ball within a medium frequency bandwidth located substantially between 10 kHz to 20 kHz for example, as only impacts of cracked balls emit acoustic energy within this bandwidth, as described in details hereinabove. The frequency bandwidth starting from about 10 kHz instead of 5 kHz in order to allow a complete filtering of the initial pulse for the reasons mentioned above gives to the overall device a satisfactory performance. It is also to be noted that use of a second order band-pass filter (10–20 kHz) will allow partial passage of components at frequencies lower than 10 kHz.

A device for sorting cracked and uncracked grinder balls comprising a device for detecting cracks in grinder balls according to the invention is divided in two parts; a mechanical assembly and an electronic circuit.

Figure 5:
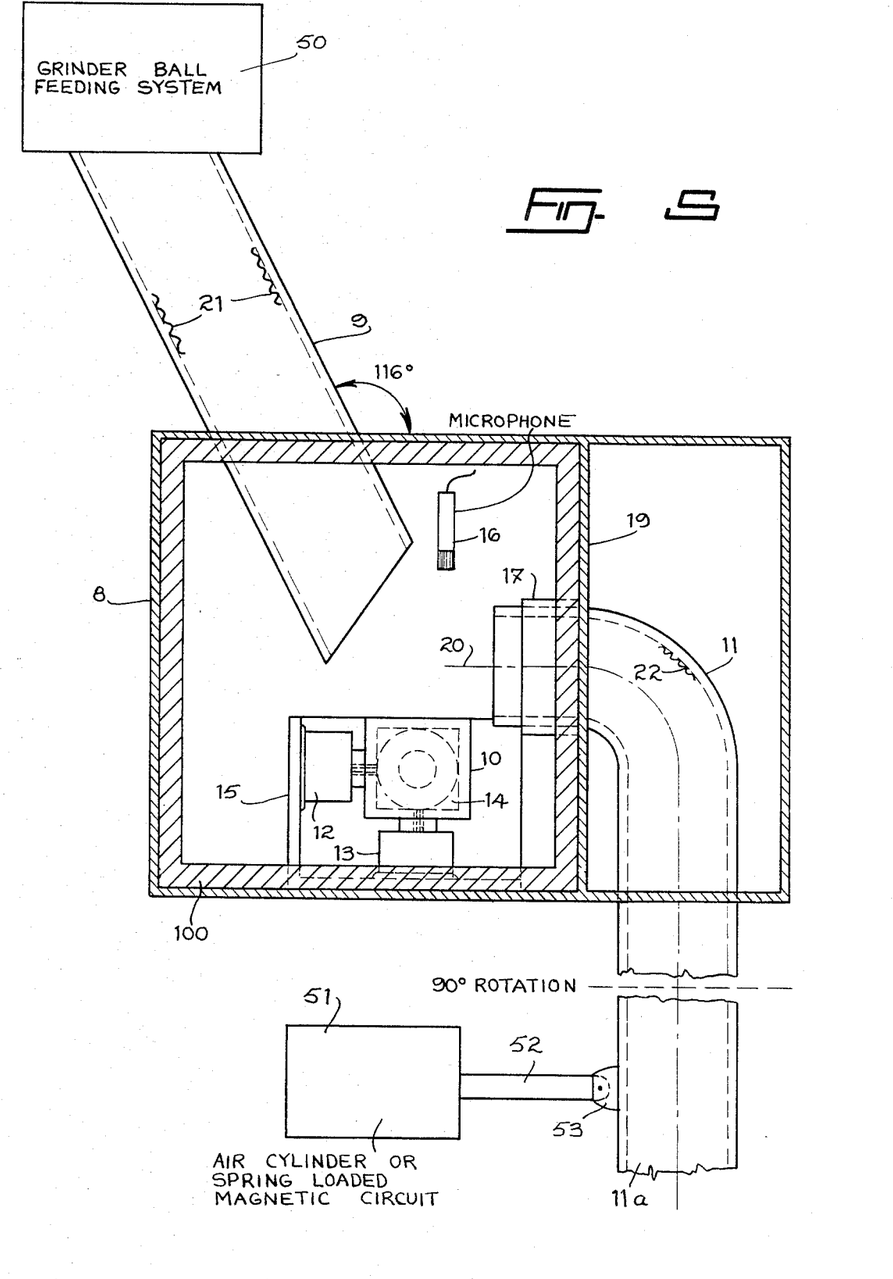
FIG. 5 illustrates an example for a mechanical assembly forming part of the detecting device according to the present invention.

FIG. 5 of the drawings shows a possible embodiment of the mechanical assembly of such a sorting device. This mechanical assembly comprises an external casing or box 8 provided with an intermediate wall 19 as shown in cross-section on FIG. 5. The walls of the casing or box 8 along with the wall 19 form a closed chamber in which can be disposed an anvil 10 and a microphone 16. This wall 19 and the box 8 can be made for example of thick steel plates. The steel plates forming the walls of the chamber in which the anvil 10 and the microphone 16 are disposed is advantageously lined inside with 1″ thick sound foam acoustic absorbent 100 shown on FIG. 5 which shields this chamber from external surrounding noises and makes it practically echo-free in order to prevent false measurements due to surrounding noises and echoes in the chamber.

In operation, the grinder balls at the end of the production line pass through an appropriate feeding system shown schematically at 50 before entering one by one at the top of a drop tube 9, roll down through the drop tube 9, hit the anvil 10, and finally exit through a deflector tube 11.

The drop tube 9 makes, as shown on FIG. 5, an angle of 116° with the top face of the casing 8. This angle gives to the balls the necessary horizontal velocity to rapidly exit through the deflector tube after the impact between the ball and the anvil 10. Of course, the mechanical assembly is designed for this purpose. The rapidity of the clearance of the balls after impact is an important aspect as the travel time between the impact and the output of the deflector tube 11 is the essential limitation of the rate of the device, i.e. the number of balls inspected per time unit. The electronic circuit is not the limiting factor, as the good or cracked diagnosis is done before the grinder ball actually leaves the anvil 10.

Another important aspect to be considered in designing the mechanical assembly is the repeatibility of the trajectory and velocity of the grinder balls in order to facilitate the calibration of the electronic circuit described hereinafter and also to increase the performance of the detecting device.

The anvil 10 consists preferably of a massive block of steel supported by three shock absorbers 12, 13 and 14 bolted on a ½" steel structure 15. These three shocks absorbers prevent a transmission of vibration to the supporting structure 15 induced by an impact between the anvil 10 and a grinder ball.

A major constraint in operating the device of the invention is the signal-to-noise ratio. Because this is an acoustical device, sources of acoustic noise, especially those occurring at the moment of impact of grinder balls and in the frequency range of cracked ball resonances have obviously to be minimized.

Of particular importance in this matter is the anvil 10. It must be designed so that the frequency of its lowest mode of resonance is much higher than cracked balls resonant frequencies (10–20 kHz). The anvil 10 has also to be mounted as mentioned above on some sort of damped suspension (the shock absorbers 13, 14 and 15 in the present case) so that when it is struck by a grinder ball, the high frequency part of the impact force is not transmitted to the supporting structure 15 and the casing 8 and therefore does not produce high frequency acoustic waves through these supporting structure and casing, which high frequency acoustic waves can disturb the measurement through the microphone 16.

For this reason and also to maximize the portion of the impact energy transmitted to the grinder ball, one would tend to make the anvil 10 as massive as possible. The limiting factor is that the resonant frequencies reduce with increasing size of the anvil 10. It is possible to increase the mass of the anvil 10 without decreasing its resonant frequency by optimizing its shape. In this respect, the sphere has the highest mass frequency product followed by the square cylinder (length equal to diameter), followed by the cube etc. . . The cylinder is probably the best compromise for an automated device but, in theory, the best target to test a particular size of grinder ball is another uncracked one of the same size. However, the cube also constitutes a very convenient compromise.

The deflector tube 11 is simply a <<L>> shaped tube rotatable about its horizontal axis 20 into a supporting member 17. Of course, the lower wall of the casing B is so designed for allowing the rotation of the deflector tube 11.

A vertical portion 11a of the deflector tube is shown 90° pivoted with respect to the portion 11 of the deflector tube to show the way used to deflect the deflector tube. An air cylinder or a spring loaded magnetic circuit 51 is used to pull through an arm or piston 52 and a fixing member 53 the vertical portion of the deflector tube (about 15° rotation about the horizontal axis 20) to deflect a cracked grinder ball to, for example, a first steel drum or releases the deflector tube to its normal vertical position to deflect uncracked grinder balls to, for example, a second steel drum.

This spring loaded magnetic circuit is operated through a coil while the air cylinder is operated through the coil of a solenoid valve. In the two cases, the coil is controlled through an electronic circuit as will be seen hereinafter.

Absorbers 21 and 22 made of rubber material can also be provided within the tubes 9 and 11, respectively, in order to reduce noise generated by the movement of the grinder balls within these two tubes.

Another possibility for conducting the grinder balls is to replace the deflector tube 11 by an appropriate system designed to generate magnetic fields acting directly on the grinder balls for conducting these balls towards their respective storing locations.

Figure 6:
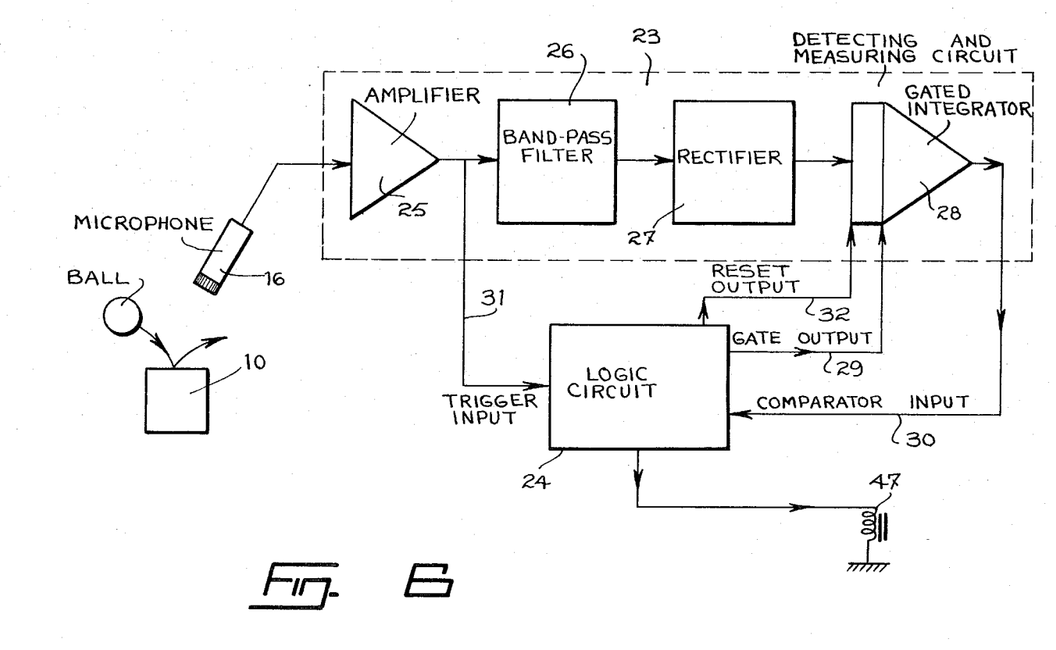
FIG. 6 is a block diagram of an electronic circuit forming part of the detecting device according to the present invention.

A block diagram of the electronic circuit of the device according to the invention is shown on FIG. 6. This electronic circuit comprises the microphone 16 (also shown on FIG. 5) a detecting and measuring circuit 23 receiving the signal from the microphone 16 which catches the acoustic wave produced by the impact between a grinder ball and the anvil 10 (also shown on FIG. 5), and a logic circuit 24 for controlling an integrator 28 of the circuit 23, and the energization of a coil 47 controlling the operation of the magnetic circuit or the solenoid valve of the air cylinder 51 shown on FIG. 5.

The microphone has preferably a flat response up to 30 kHz and is located in the above defined chamber as near as possible of the trajectory of the grinder balls and of the point of impact of these grinder balls on the anvil 10, as shown on FIG. 5. As also illustrated on FIG. 5, the microphone 16 is positioned to point downward in order to prevent building up of dust and other pollutants on its membrane.

Referring back to FIG. 6, the circuit 23 comprises an amplifier 25 for amplifying the sound signal from the microphone 16. The amplified signal at the output of the amplifier 25 is supplied to the input of a band-pass filter 26 and to a trigger input of the logic circuit 24.

The band-pass filter 26 which is preferably of the second order has a transmission bandwidth selected between 10 kHz and 20 kHz, thereby allowing passage of the above defined mid-range resonance frequencies characterizing cracked grinder balls impacts, and filtering off of resonances frequencies typical of uncracked grinder ball impacts and of frequency components due to the initial pulse defined hereinbefore and to the resonances of the anvil 20.

When a cracked ball is tested, the signal components transmitted through the band-pass filter 26 (10–20 kHz signal components) are rectified by a rectifier 27, and the rectified output signal (see curve B of FIG. 8) of the rectifier 17 is integrated through a gated integrator 28. This integrator 28 integrates the output rectified signal over a time window defined by a gate signal supplied to the integrator 28 by the logic circuit 24 through its gate output 29. Of course, before each integrating time window the logic circuit 24 resets the integrator 28 through its reset output 32. The integrated voltage at the output of the integrator 28 (see curve G of FIG. 8) is supplied to a comparator input 30 of the logic circuit 24 which compares this integrated output voltage to an adjustable reference to determine whether the ball is cracked or not and to control energization of the coil 47 accordingly.

An example for the logic circuit 24 which carries out the measurement and control the energization of the coil 47 will be described with reference to FIG. 7.

Figure 7:
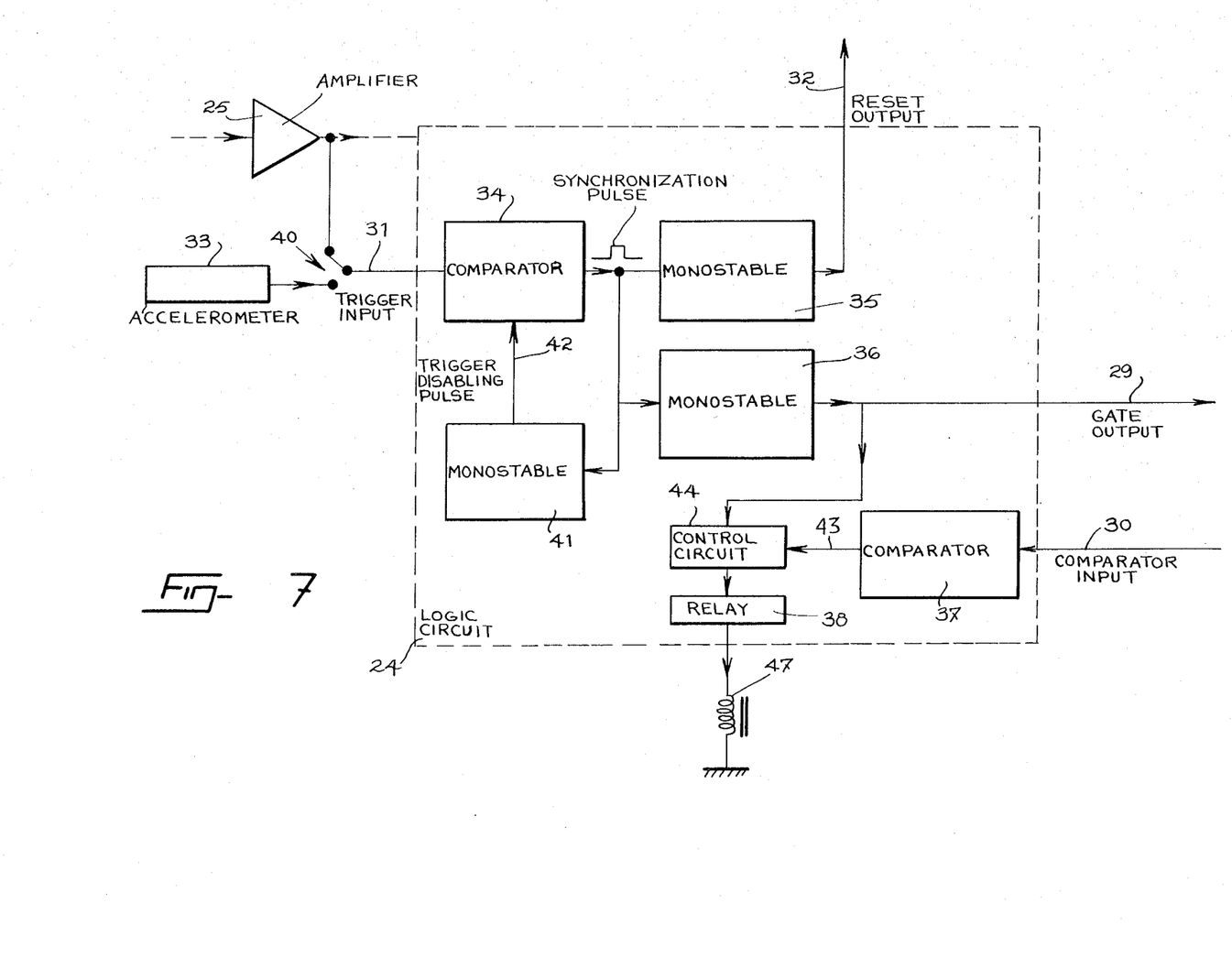
FIG. 7 is a block diagram showing in more details the structure of a logic circuit forming part of the electronic circuit block diagram of FIG. 6.

As shown on FIG. 7, the logic circuit 24 comprises a comparator 34 used to generate a synchronisation pulse (see curve C on FIG. 8) to start a sequence of measurement of the device of the invention. The input of this comparator 34 corresponds to the trigger input 31 of the logic circuit 24 and is connected to the output of the amplifier 25 amplifying the signal generated by the microphone 16 (see FIG. 6). When the level of the signal at the output of the amplifier 25 reaches a comparison level (see curve A of FIG. 8) of the comparator 34, this comparator produces a <<high>> level output signal provided there is no trigger disabling pulse at the output of a monostable 41 as will be seen hereinafter. This comparison level is selected in order that only the above defined initial pulse upon a grinder ball impact can trigger the comparator 34. Consequently, the comparator 34 produces a high level output signal during only the time of occurrence of the initial pulse and therefore generates a synchronization pulse at its output when such a pulse occurs. In order to avoid any false triggering due to spurious noise sensed by the microphone, the trigger input 31 of the comparator 34 may be supplied by an accelerometer 33 screwed on the anvil 10 (FIG. 5) by appropriately selecting the position of a switch 40. The accelerometer 33 supplies a pulse upon impact between a grinder ball and the anvil 10 for allowing the comparator 34 to generate a synchronization pulse as explained above. The use of an accelerometer therefore eliminates any false triggering on spurious noise which occasionally occurs with acoustic triggering.

Upon occurrence of the trailing edge of a synchronization pulse at the output of the comparator 34, a monostable 35 supplies a reset pulse (see curve D of FIG. 8) on the reset output 32 in order to hold on reset the integrator 28 for about 1 ms and also to allow a more efficient blanking out of the initial pulse upon impact and a monostable 36 generates a gate pulse extending about 10 ms after the end of the reset pulse (see curve E of FIG. 8) and supplied through the gate output 29 to the gated integrator 28 for defining the time gate of integration of this integrator. The end of this gate pulse is positioned just before the occurrence of a second collision between the ball and the anvil 10 due to the recoil of the anvil bouncing back on the grinder ball. The synchronization pulse at the output of the comparator 34, is also supplied to a monostable 41 provided for generating at its output 42 a trigger disabling pulse (see curve F of FIG. 8) in response to the trailing edge of the synchronization pulse, this disabling pulse being applied to an input of the comparator 34. The trigger disabling pulse inhibits the output of the comparator 34 during a period of time extending up to 100 ms after the end of the gate pulse. Such a disabling pulse prevents the comparator 34 to generate a synchronization pulse when retriggered by the second collision between the grinder ball and the anvil 10 due to the recoil of the anvil bouncing back on the grinder ball (see A1 on curve A of FIG. 8 for example) or by any other spurious noise.

A comparator 37 receives, during the above defined gate pulse, through the comparator input 30 the integrated signal at the output of the integrator 28 (see FIG. 6) and compares this integrated signal with a reference which is adjustable and memorized in this comparator 37. If the integrated signal at the output of the integrator 28 reaches the level of the reference during the gate pulse generated by the monostable 36, the output of the comparator 37 is used by a control circuit 44 which is preferably provided to energize the coil 47 through a relay 38 for the reasons exposed hereinafter (see curves G and H of FIG. 8).

As briefly stated above, the output of the comparator 37 is used by the control circuit 44 to control the energization of the relay 38, which control circuit 44 energizes or de-energizes the coil of the relay 38 at the end of the gate pulse at the output of the monostable 36 according to the output 43 of the comparator 37 which indicates that the level of the integrated signal at the output of the integrator 18 is higher or lower than the reference memorized in the comparator 37 and therefore if the actually tested grinder ball is cracked or not. This allows advantageously a deflection of the deflector tube 11 during a lapse of time in which no measurement is made and therefore in which the generation of noise by the deflection of the tube 11 cannot disturb the measurement.

After the end of the trigger disabling pulse at the output of the monostable 41 the above described sequence of operation is repeated through the logic circuit 24 when the trigger input 31 reaches the trigger comparison level memorized in the comparator 34, after impact between a grinder ball and the anvil 10.

Figure 8:
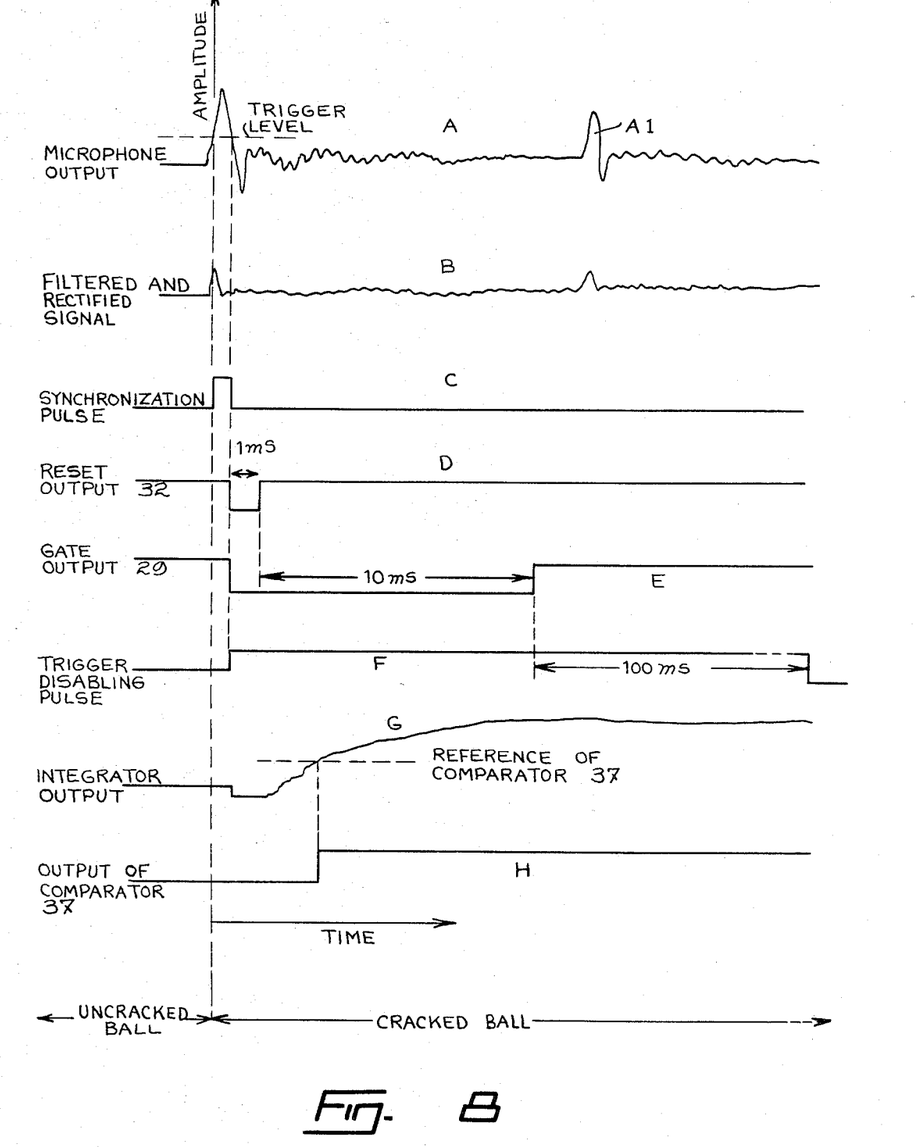
FIG. 8 illustrates waveforms for a cracked grinder ball at different points of the block diagrams of FIGS. 6 and 7, and depicts a sequence of events.

Of course, the pulses shown on curves D to F on FIG. 8 may be either high level or low level pulses according to the specific structure of the integrator 28 and the comparator 34.

Although the present invention has been described by way of a preferred embodiment directed particularly to detection of cracks in grinder balls, it should be noted that an analysis similar to the one made above can be carried out for other metal pieces having different shapes in view of designing an appropriate detecting and sorting device of the kind described hereinbefore. Of course, any modification in the use and structure of the preferred embodiment defined in the present disclosure, within the scope of the appended claims, is not deemed to change or alter the nature and inventive idea of the present invention.

What is claimed is:

1. A device for detecting a crack in a metal piece comprising:
   anvil means;
   means for producing an impact between the metal piece and the anvil means, said impact generating an acoustic wave formed of a plurality of components, one of said components being produced by vibrations of said metal piece and having a frequency indicating a cracked or uncracked state of the metal piece;
   means for sensing and measuring the energy of said one component of said generated acoustic wave within a predetermined time gate and within a predetermined frequency bandwidth; and
   means for determining if said metal piece is cracked or uncracked in accordance with said measured energy;
   said anvil means being designed so that its vibrations generated by the impact produce no acoustic wave component at a frequency located within said predetermined frequency bandwidth in order to prevent influence on said energy measurement of any component of said generated acoustic wave produced by the anvil means.

2. The detecting device of claim 1, wherein said predetermined frequency bandwidth corresponds to a range of vibration resonance frequencies characterizing cracked metal pieces similar to said metal piece.

3. The detecting device of claim 1, wherein said detecting device comprises a supporting structure and said anvil means comprise a massive metal piece fixedly mounted through shock absorbing means on said supporting structure, said shock absorbing means preventing vibration of the supporting structure upon said impact and therefore preventing influence on the crack detection by said vibration of the supporting structure.

4. The detecting device of claim 3, wherein said massive piece has a lowest vibration resonance mode occurring at a frequency higher than the highest frequency of said predetermined frequency bandwidth, whereby the crack detection is not influenced by vibration resonance modes of said anvil means.

5. The detecting device of claim 1, wherein said anvil means are fixed, and wherein said impact producing means comprises means for guiding said metal piece towards said anvil means while giving speed to said metal piece to produce the impact between the metal piece and the anvil means.

6. The detecting device of claim 5, wherein said metal piece is a grinder ball, and said guiding means comprise a drop tube having a geometrical axis positioned with a certain angle with respect to a vertical axis.

7. The detecting device of claim 1, wherein said sensing and measuring means comprise an acoustic detector disposed close to a point of impact between the metal piece and the anvil means, said acoustic detector comprising means for generating a signal representative of said generated acoustic wave.

8. The detecting device of claim 7, wherein said sensing and measuring means further comprise:
   means for amplifying said signal generated through the acoustic detector;
   a band-pass filter for filtering said amplified signal, said band-pass filter having a transmission frequency bandwidth corresponding to said predetermined frequency bandwidth;
   means for rectifying said filtered amplified signal; and
   means for integrating the rectified filtered amplified signal during said predetermined time gate, said integrating means delivering an output signal representative of the energy within said predetermined time gate and within said predetermined frequency bandwidth of said one component of the acoustic wave generated by the impact.

9. The detecting device of claim 8, wherein said determining means comprise means for comparing the output signal from said integrating means with a reference, said comparing means delivering a signal indicating if said metal piece is cracked or uncracked.

10. The detecting device of claim 8, wherein said sensing and measuring means comprise means for resetting said integrating means and for generating a gate signal, and means for triggering said resetting and gate signal generating means upon occurrence of said impact between the metal piece and the anvil means, said gate signal being applied to said integrating means and defining said predetermined time gate.

11. The detecting device of claim 10, wherein said triggering means comprise means responsive to said amplified signal for delivering a triggering signal to said resetting and gate signal generating means upon occurrence of an initial pulse forming part of said acoustic wave generated by said impact.

12. The detecting device of claim 11, wherein said sensing and measuring means comprise means acting on said triggering signal delivering means for preventing retriggering of said resetting and gate signal generating means during a predetermined time duration after said delivering of a triggering signal upon occurrence of said initial pulse, said predetermined time duration being longer than said predetermined time gate, whereby retriggering of said resetting and gate signal generating means by spurious noises or by a second impact between the metal piece and the anvil means due to bouncing back of said anvil means on said metal piece is avoided.

13. The detecting device of claim 10, wherein said triggering means comprise an accelerometer secured on said anvil means for supplying a triggering signal to said resetting and gate signal generating means upon occurrence of said impact between the metal piece and the anvil means.

14. The detecting device of claim 13, wherein said sensing and measuring means comprise means for preventing retriggering through said accelerometer of said resetting and gate signal generating means during a predetermined time duration after said supplying by said accelerometer of a triggering signal upon occurrence of said impact, said predetermined time duration being longer than said predetermined time gate, whereby retriggering of said resetting and gate signal generating means by a second impact between the metal piece and the anvil means due to bouncing back of said anvil means on said metal piece is avoided.

15. The detecting device of claim 7, comprising a chamber defining an inner space in which are disposed said acoustic detector and said anvil means, said chamber comprising means for acoustically insulating said inner space from outside noises and for preventing generation of echos by said acoustic wave within said inner space, whereby the crack detection is not disturbed by said outside noises and said echos.

16. The detecting device of claim 1, wherein said sensing and measuring means comprise synchronization means for starting an energy measuring operation upon occurrence of said impact between the metal piece and the anvil means, and for controlling said energy measuring operation.

17. A device for sorting cracked and uncracked metal pieces having a same shape and made of a same metal, comprising:
   a detecting device as defined in claim 1;
   means for supplying in sequence to said impact producing means of the detecting device said metal pieces for detecting through said detecting device if these metal pieces are cracked or uncracked; and
   means controlled by said determining means of the detecting device for conducting each cracked metal piece from said detecting device towards first storing means and for conducting each uncracked metal piece from said detecting device towards second storing means.

18. A method for detecting a crack in a metal piece comprising the steps of:
   producing an impact between the metal piece and anvil means, said impact generating an acoustic wave formed of a plurality of components, one of said components being produced by vibrations of said metal piece and having a frequency indicating a cracked or uncracked state of the metal piece;
   sensing and measuring the energy of said one component of said generated acoustic wave within a predetermined time gate and within a predetermined frequency bandwidth, and
   determining if said metal piece is cracked or uncracked in accordance with said measured energy;

said anvil means being designed so that its vibrations generated by the impact produce no acoustic wave component at a frequency located within said predetermined frequency bandwidth in order to prevent influence on said energy measurement of any component of said generated acoustic wave produced by the anvil means.

19. The method of claim 18, wherein said predetermined frequency bandwidth corresponds to a range of vibration resonance frequencies characterizing cracked metal pieces similar to said metal piece.

20. The method of claim 18, wherein the sensing and measuring step comprises the steps of:
sensing said generated acoustic wave through an acoustic detector delivering a signal representative of this acoustic wave;
amplifying the signal delivered by the acoustic detector;
band-pass filtering said amplified signal to allow only transmission of any component of said amplified signal having a frequency located within said predetermined frequency bandwidth;
rectifying said filtered amplified signal; and
integrating said rectified, filtered amplified signal during said predetermined time gate for producing an integrated signal representative of the energy within said predetermined time gate and within said predetermined frequency bandwidth of said one component of the generated acoustic wave.

21. The method of claim 20, wherein said determining step comprise the step of comparing said integrated signal with a reference to produce a signal indicating if said metal piece is cracked or uncracked.

22. The method of claim 20, wherein said anvil means and said acoustic detector are disposed within an echo-free chamber provided for acoustically insulating the acoustic detector from outside noises.

23. The method of claim 18, comprising the step of synchronizing said measuring step in accordance with a moment of occurrence of said impact between the metal piece and the anvil means.

24. A method for sorting cracked and uncracked metal pieces having a same shape and made of a same metal; comprising the steps of:
carrying out in sequence for each metal piece the detecting method of claim 18, for detecting if this metal piece is cracked or uncracked; and
conducting each metal piece found cracked by said determining step of the detecting method towards first storing means, and conducting each metal piece found uncracked by said determining step of the detecting method towards second storing means.

* * * * *